(12) United States Patent
D'Anello et al.

(10) Patent No.: US 8,592,583 B2
(45) Date of Patent: *Nov. 26, 2013

(54) PROCESS FOR THE PREPARATION OF 5-(2-AMINO-PYRIMIDIN-4-YL)-2-ARYL-1H-PYRROLE-3-CARBOXAMIDES

(75) Inventors: Matteo D'Anello, Novate Milanese (IT); Marco Re, Novara (IT)

(73) Assignee: Nerviano Medical Sciences, Nerviano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/505,357

(22) PCT Filed: Oct. 27, 2010

(86) PCT No.: PCT/EP2010/066241
§ 371 (c)(1),
(2), (4) Date: May 1, 2012

(87) PCT Pub. No.: WO2011/054714
PCT Pub. Date: May 12, 2011

(65) Prior Publication Data
US 2012/0220771 A1    Aug. 30, 2012

(30) Foreign Application Priority Data
Nov. 4, 2009 (EP) .................................... 09175063

(51) Int. Cl.
*C07D 401/00* (2006.01)
(52) U.S. Cl.
USPC ........................................................ 544/331
(58) Field of Classification Search
USPC ........................................................ 544/331
See application file for complete search history.

(56) References Cited

U.S. PATENT DOCUMENTS

2005/0261331 A1* 11/2005 Nielsen et al. ................ 514/300

FOREIGN PATENT DOCUMENTS

WO   WO 2007/110344 A1   10/2007
WO   WO 2009/133170 A1   11/2009

OTHER PUBLICATIONS

Morrison, Organic Chemistry 4th Ed., Allyn and Bacon, Inc., p. 598 (1983).*
Morrison, Robert. Organic Chemistry 4th Ed. Allyn and Bacon, Inc. Boston: 1983.*
Vanotti E. et al., "Regioselective Halogenation of Aminopyrimidinyl-Pyrrole Carboxylic Acid Derivatives", *Tetrahedron* 65(50):10418-10423 (2009).
Declerck V. et al., "Sequential *aza*-Baylis-Hillman/Ring Closing Metathesis/Aromatization as a Novel Route for the Synthesis of Substituted Pyrroles", *Journal of Organic Chemistry* 69(24):8372-8381 (2004).
Weber J-V et al., "Reactivity of Biheterocyclic Phenanthrene Analogs Toward Acetylation and Lithiation Agents", *Journal of Heterocyclic Chemistry* 20(1):61-64 (Jan.-Feb. 1983), together with an English-language abstract.
Gupton J.T. et al., "The Preparation of Heterocyclic Appended Vinylogous Iminium Salts and Their Application to the Regioselective Preparation of Biheterocyclic Systems", *Heterocycles* 27(2):689-702 (1998).
Domagala J.M. et al., "New 7-Substituted Quinolone Antibacterial Agents. II. The Synthesis of 1-Ethyl-1,4-Dihydro-4-Oxo-7-(Pyrazolyl, Isoxazolyl, and Pyrimidinyl)-1,8-Naphthyridine and Quinolone-3-Carboxylic Acids", *J. Heterocyclic Chem.* 26:1147-1158 (Jul.-Aug. 1989).
Selwood D.L. et al., "Synthesis and Biological Evaluation of Novel Pyrazoles and Indazoles as Activators of the Nitric Oxide Receptor, Soluble Guanylate Cyclase", *J. Med. Chem.* 44(1):78-93 (2001).
Chu D.T.W. et al., "An Alternative Synthesis of Temafloxacin, a Potent Antibacterial Agent", *Can. J. Chem.* 70:1323-1327 (1992).
Mansour T.S. et al., "Decarboxylative Carbon Acylation of Malonates with Aminoacylimidazolides Mediated by Lewis Acids", *Synthetic Communications* 20(5):773-781 (1990).
International Search Report dated Mar. 15, 2011 received from the European Patent Office from related International Application No. PCT/EP2010/066241.

* cited by examiner

*Primary Examiner* — Noble Jarrell
*Assistant Examiner* — Laura Daniel
(74) *Attorney, Agent, or Firm* — Scully, Scott, Murphy & Presser, P.C.

(57) ABSTRACT

The invention relates to a process for the preparation of 5-(2-amino-pyrimidin-4-yl)-2-aryl-1H-pyrrole-3-carboxamides and to the useful intermediate compounds of such process. The process allows to obtain the desired products in high yields and purity. The synthesis is starting from the coupling of an acetal with a beta-ketoester; the resultant compound is acetylated and then reacted with a dialkyl acetal of N,N-dimethylformamide to give an intermediate which is cyclized to 5-(2-amino-pyrimidin-4-yl)-2-aryl-1H-pyrrole-3-carboxylic ester; the carboxylic ester is then hydrolyzed and the resultant carboxylic acid is finally condensed with an appropriate form of ammonia to give the desired carboxamide. The compounds prepared according to the process of the invention are endowed with protein kinase inhibiting activity and, more particularly, Cdc7 or Cdc7/Cdks inhibiting activity. The compounds are useful in the treatment of a variety of cancers, cell proliferative disorders and diseases associated with protein kinases.

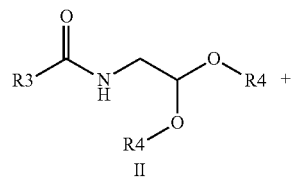

II

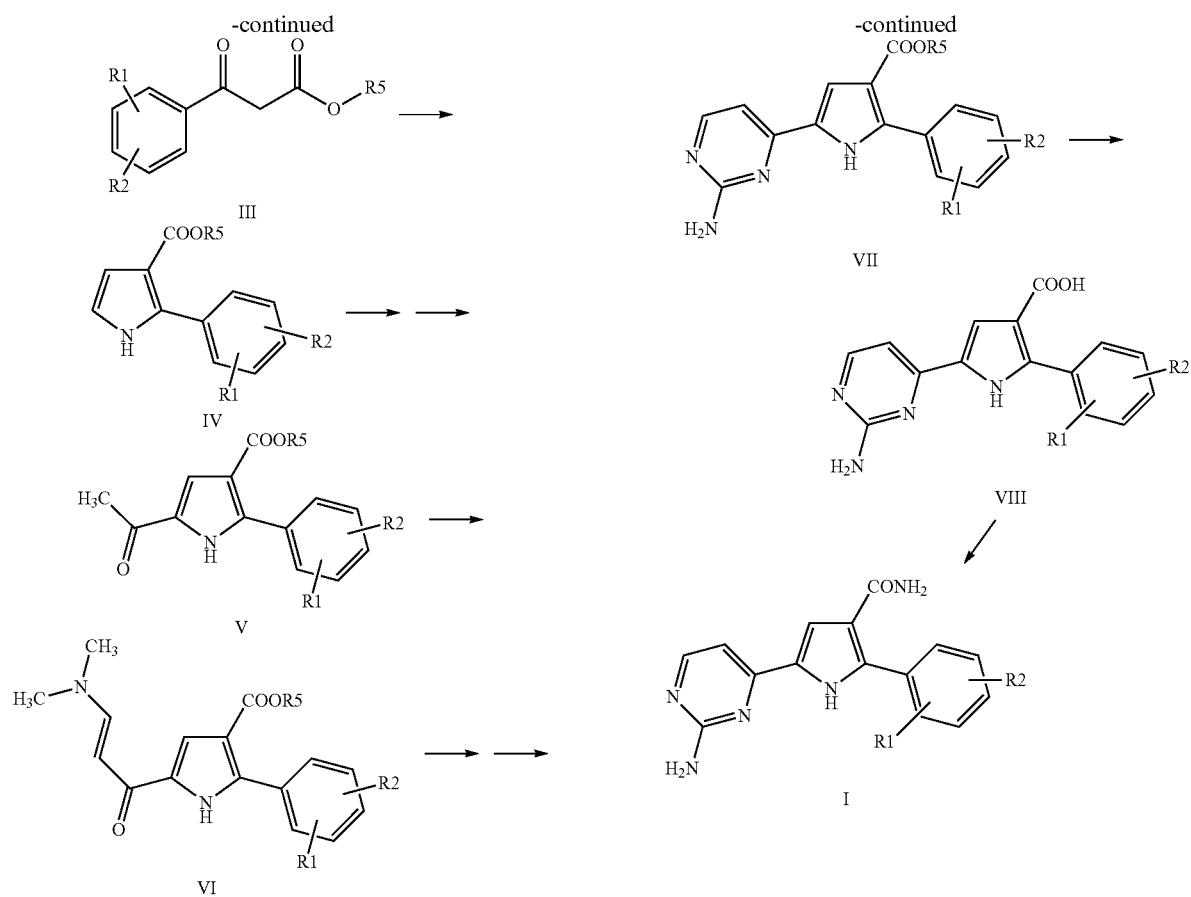
17 Claims, No Drawings

PROCESS FOR THE PREPARATION OF 5-(2-AMINO-PYRIMIDIN-4-YL)-2-ARYL-1H-PYRROLE-3-CARBOXAMIDES

BACKGROUND OF THE DISCLOSURE

The present invention relates to a process for the preparation of 5-(2-amino-pyrimidin-4-yl)-2-aryl-1H-pyrrole-3-carboxamides and to the useful intermediate compounds of such process.

WO2007110344 describes and claims heteropentacycles, processes for their preparation, pharmaceutical compositions comprising them and their use as therapeutic agents, particularly in the treatment of cancer and cell proliferation disorders.

Such compounds are endowed with protein kinase inhibiting activity and, more particularly, Cdc7 or Cdc7/Cdks inhibiting activity.

More specifically, the compounds prepared according to this invention are useful in the treatment of a variety of cancers and of cell proliferative disorders.

The compounds may be also active as inhibitors of other protein kinases and thus be effective in the treatment of diseases associated with other protein kinases.

These compounds, and analogues thereof, can be prepared according to a known chemical process comprising, essentially, the condensation reaction between a carboxylic acid derivative with either an activated form of ammonia, or with an amine to give the desired amide. Such carboxylic acid derivative, in its turn, is prepared according to a procedure comprising the coupling of a haloketone with a beta-ketoester, a Hantzsch reaction and a hydrolysis. For reference, this process is described in the above mentioned patent application WO2007110344.

In this respect, we have now surprisingly found that said heteropentacycle compounds can be advantageously prepared through a process which allows to obtain the desired products in higher yields.

BRIEF SUMMARY OF THE DISCLOSURE

Therefore, it is a first object of the present invention a process for preparing a 5-(2-amino-pyrimidin-4-yl)-2-aryl-1H-pyrrole-3-carboxamide of the formula (I):

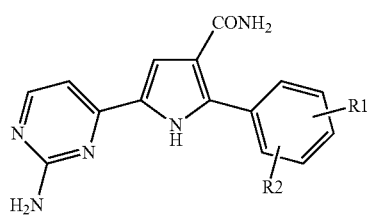

wherein R1 and R2 independently represent hydrogen, halogen, $C_1$-$C_6$ alkyl, ($C_1$-$C_6$) alkoxy, cycloalkyl, aryl or nitro group, which process comprises:

a) coupling an acetal of formula (II):

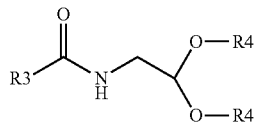

wherein R3 is $C_1$-$C_6$ alkyl and both R4 are independently $C_1$-$C_6$ alkyl or taken together are an alkylene chain having 2 or 3 carbon atoms and forming a cyclic acetal, with a beta-ketoester or a salt thereof of formula (III):

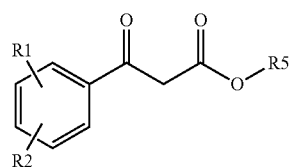

wherein R1 and R2 are as defined above and R5 is $C_1$-$C_6$ alkyl, first under acidic conditions and then under nucleophilic conditions;

b) acetylating the resultant compound of the formula (IV):

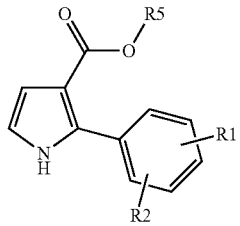

wherein R1, R2 and R5 are as defined above, with an acetyl halide or acetic anhydride in the presence of a Lewis acid;

c) reacting the resultant compound of formula (V):

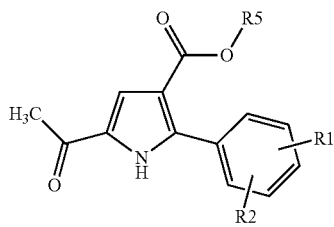

wherein R1, R2 and R5 are as defined above, with a $C_1$-$C_6$ dialkyl acetal of N,N-dimethyl formamide;

d) reacting the resultant enaminone of formula (VI):

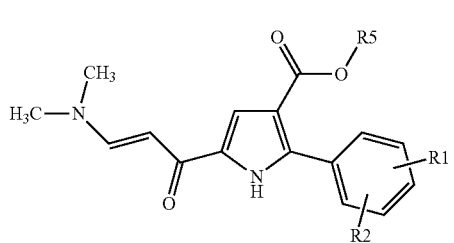

wherein R1, R2 and R5 are as defined above, with guanidine or a salt thereof;

e) hydrolyzing the carboxylic ester group of the resultant compound of formula (VII):

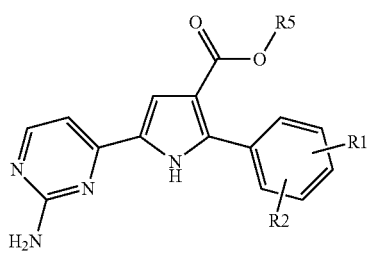

wherein R1, R2 and R5 are as defined above;

f) condensing the carboxylic acid group of the resultant compound of formula (VIII):

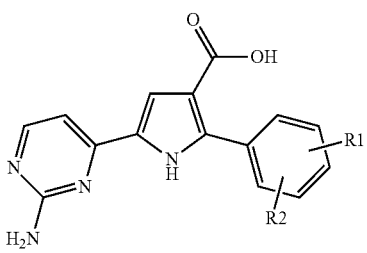

wherein R1 and R2 are as defined above, with a form of ammonia, to give the carboxamide of formula (I) as defined above; and, if desired, converting it into a pharmaceutically acceptable salt.

Any intermediates and/or the final compounds may be isolated and purified using conventional procedures, for example chromatography and/or crystallization and salt formation.

The carboxamides of the formula (I) as defined above can be converted into pharmaceutically acceptable salts. The carboxamides of the formula (I) as defined above, or the pharmaceutically acceptable salts thereof, can be subsequently formulated with a pharmaceutically acceptable carrier or diluent to provide a pharmaceutical composition.

The new process is shown in Scheme 1.

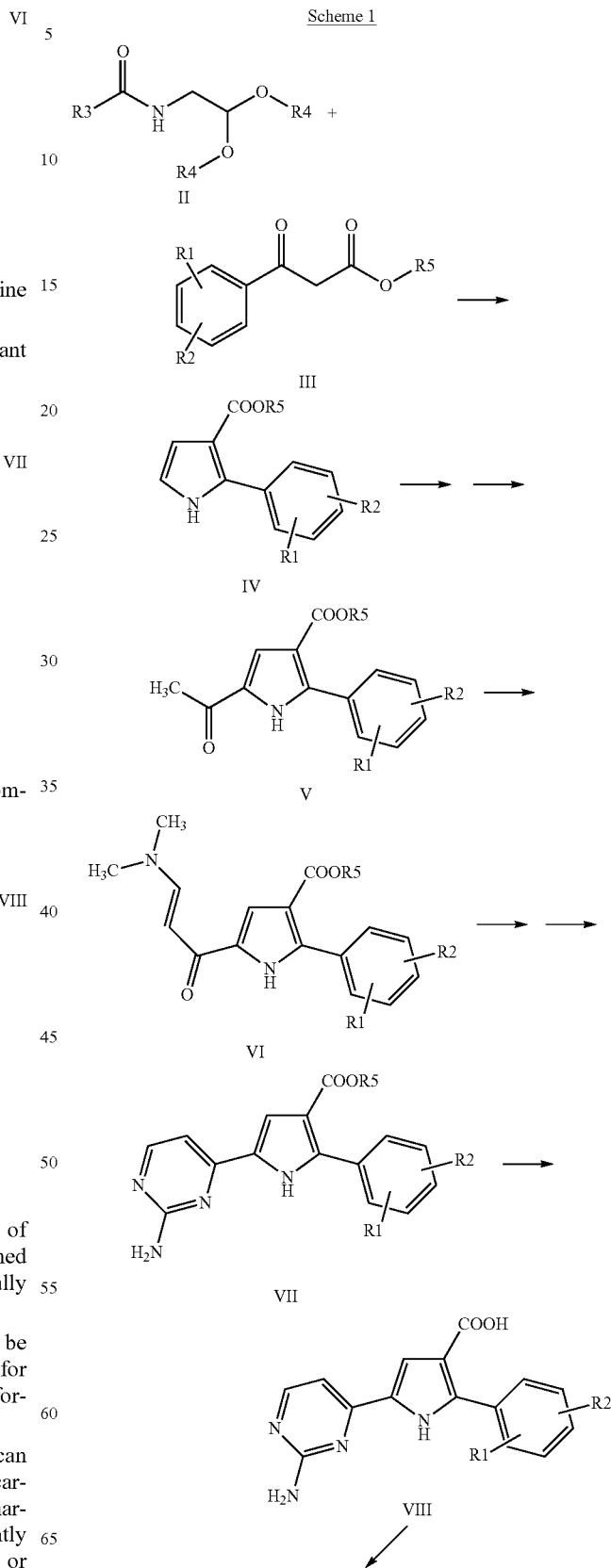

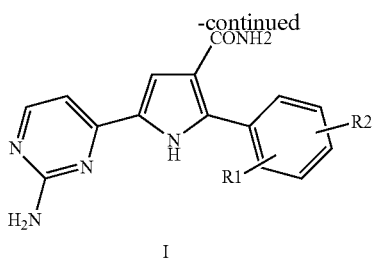

wherein R1, R2, R3, R4 and R5 are as defined above.

Moreover, it is another object of the present invention some useful intermediate compounds as well as the processes for their preparation.

DETAILED DESCRIPTION OF THE DISCLOSURE

In the present specification, the terms
"halogen" refers to bromo, chloro, iodo or fluoro, more preferably chloro or fluoro;
"$C_1$-$C_6$ alkyl" refers to straight or branched saturated aliphatic hydrocarbyl groups having from 1 to 6 carbon atoms; this term is exemplified by groups such as methyl, ethyl, n-propyl, iso-propyl, n-butyl, isobutyl, sec-butyl, t-butyl, n-pentyl, n-hexyl, and the like;
"$C_1$-$C_6$ alkoxy" refers to straight or branched saturated aliphatic hydrocarbyl groups having from 1 to 6 carbon atoms linked to rest of the molecule through an oxygen atom; this term is exemplified by groups such as methoxy, ethoxy, n-propoxy, isopropoxy, and the like;
"cycloalkyl" refers to cyclic alkyl groups of from 3 to 10 carbon atoms having single or multiple cyclic rings including, by way of example, adamantyl, cyclopropyl, cyclobutyl, cyclopentyl, cyclohexyl, cyclooctyl and the like;
"aryl" refers to an aromatic carbocyclic group of from 6 to 14 carbon atoms having a single ring (e.g. phenyl) or multiple condensed rings (e.g. naphthyl or anthryl) which condensed rings may or may not be aromatic (e.g. 2-benzoxazolinone, 2H-1,4-benzoxazin-3(4H)-one-7-yl, and the like) provided that the point of attachment is at an aromatic carbon atom; preferred aryls include phenyl and naphthyl; in the name of the compounds of the formula I, aryl is a phenyl substituted with $R_1$ and $R_2$ as defined above;
"nitro" refers to the group —$NO_2$;
"cyclic acetal" refers to a compound of formula (II) as defined above, wherein R3 is $C_1$-$C_6$ alkyl and both R4 taken together are an alkylene chain having 2 or 3 carbon atoms, that is:

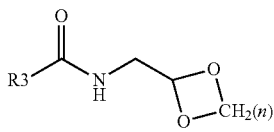

wherein R3 is as above defined and n is 2 or 3.

A preferred class of compounds of formula (I) prepared with the process of the present invention are the compounds wherein R1 and R2 independently represent hydrogen, methyl groups or fluoro or chloro atoms, more preferably R1 and R2 are both chloro atoms, even more preferably R1 and R2 are at 2, 6 positions on the benzene ring.

Preferred specific compounds of formula (I) are the compounds listed below:

5-(2-amino-pyrimidin-4-yl)-2-phenyl-1H-pyrrole-3-carboxylic acid amide;

5-(2-amino-pyrimidin-4-yl)-2-o-tolyl-1H-pyrrole-3-carboxylic acid amide;

5-(2-amino-pyrimidin-4-yl)-2-(4-fluoro-2-methyl-phenyl)-1H-pyrrole-3-carboxylic acid amide;

5-(2-amino-pyrimidin-4-yl)-2-(2,3-dimethyl-phenyl)-1H-pyrrole-3-carboxylic acid amide;

5-(2-amino-pyrimidin-4-yl)-2-(2,3-difluoro-phenyl)-1H-pyrrole-3-carboxylic acid amide;

5-(2-amino-pyrimidin-4-yl)-2-(2,4-difluoro-phenyl)-1H-pyrrole-3-carboxylic acid amide;

5-(2-amino-pyrimidin-4-yl)-2-(2,5-difluoro-phenyl)-1H-pyrrole-3-carboxylic acid amide;

5-(2-amino-pyrimidin-4-yl)-2-(2-chloro-phenyl)-1H-pyrrole-3-carboxylic acid amide;

5-(2-amino-pyrimidin-4-yl)-2-(2-chloro-4-fluoro-phenyl)-1H-pyrrole-3-carboxylic acid amide;

5-(2-amino-pyrimidin-4-yl)-2-(2,4-dichloro-phenyl)-1H-pyrrole-3-carboxylic acid amide;

5-(2-amino-pyrimidin-4-yl)-2-(2-fluoro-4-methyl-phenyl)-1H-pyrrole-3-carboxylic acid amide;

5-(2-amino-pyrimidin-4-yl)-2-(2,3-dichloro-phenyl)-1H-pyrrole-3-carboxylic acid amide;

5-(2-amino-pyrimidin-4-yl)-2-(2-fluoro-3-methoxy-phenyl)-1H-pyrrole-3-carboxylic acid amide and 5-(2-amino-pyrimidin-4-yl)-2-(2-fluoro-4-chloro-phenyl)-1H-pyrrole-3-carboxylic acid amide.

A more preferred class of compounds of formula (I) are the compounds wherein wherein R1 and R2 are chloro atoms.

The most preferred comompound of formula (I) is 5-(2-amino-pyrimidin-4-yl)-2-(2,4-dichloro-phenyl)-1H-pyrrole-3-carboxylic acid amide.

As stated above, the present invention also provides an intermediate compound of formula (IV)':

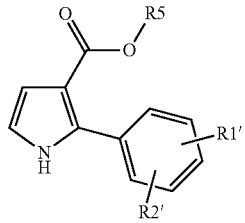

wherein R1' and R2' are halogen atoms and R5 is as defined above.

It is a further object of the present invention a process for preparing an intermediate compound of formula (IV) as defined above, by coupling a dialkyl acetal of formula (II) as defined above with a beta-ketoester or a salt thereof of formula (III) as defined above, first under acidic conditions and then under nucleophilic conditions.

The present invention also provides an intermediate compound of formula (V):

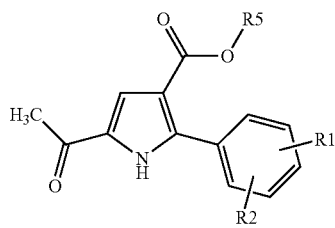

wherein R1, R2 and R5 are as defined above.

It is still another object of the present invention a process for preparing an intermediate compound of formula (V) as defined above, by treatment of a compound of the formula (IV) as defined above with an acetyl halide or acetic anhydride in the presence of a Lewis acid.

It is also provided an intermediate enaminone of formula (VI):

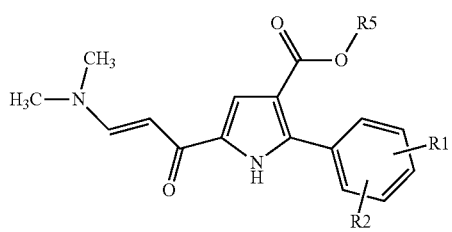

wherein R1, R2 and R5 are as defined above.

It is still another object of the present invention a process for preparing an intermediate enaminone of formula (VI) as defined above, characterized by the steps from a) to c) as defined above.

It is still another object of the present invention a process for preparing an intermediate enaminone of formula (VI) as defined above, by reaction of the compound of the formula (V) as defined above with a dialkyl acetal of N,N-dimethyl formamide.

According to step a) the coupling of a dialkyl acetal of formula (II) with a beta-ketoester or a salt thereof of formula (III) to give a compound of formula (IV) is performed under strong acidic conditions, e.g. using trifluoroacetic acid (TFA) as solvent. Preferably, the beta-ketoester is a salt, more preferably the beta-ketoester is an imidazole salt. The reaction can be carried out from a temperature between room temperature and reflux temperature, preferably at a temperature between room temperature and 60°. Then the reaction mixture is treated under nucleophilic conditions in a hydroalcoholic solution, e.g. ethanol/sodium hydroxide.

According to step b) the acetylation of a compound of the formula (IV) to give the corresponding acetylated derivative of formula (V) is performed with acetyl chloride in the presence of a Lewis acid, for instance aluminum trichloride or titanium tetrachloride at a temperature of from –5° C. to room temperature in an organic solvent, e.g. dichloromethane. A similar reaction is described in *J.Het.Chem.* 1983, 20, 61.

According to step c) the reaction of a compound of formula (V) with a dialkyl acetal of N,N-dimethylformamide, for instance the dimethyl acetal or diisopropyl acetal, can be carried out from a temperature between room temperature and reflux temperature. Preferably the reaction is carried out at a temperature of from 60° to 100° C., in an organic solvent such as, e.g., dioxane. An analogous transformation was described, for instance, in *Heterocycles* 1998, 47, 689.

According to step d) the reaction of a compound of the formula (VI) with guanidine or a salt thereof, can be carried out at a temperature between room temperature and reflux temperature. Preferably the guanidine salt is hydrochloride or carbonate. Preferably the reaction is carried out at a temperature of from 60° C. to reflux, in an organic solvent such as, e.g., ethanol. Such kind of conversion is described in the scientific literature, for example in *J.Het.Chem.* 1989, 26, 1147.

According to step e) the hydrolysis of a compound of formula (VII) is carried out with methods well known to the experts in the art, preferably it is carried out in a mixture of diluted NaOH and an organic solvent such as, e.g. dioxane, at a temperature of from 60° C. to reflux.

According to step f) the condensation of a compound of formula (VIII) is carried out with methods well known to the experts in the art, preferably it is carried out in an organic solvent such as, e.g. dioxane, at a temperature of from room temperature to 80° C., with a condensing agent such as, e.g. carbonyl diimidazole, and an appropriate source of ammonia such as aqueous ammonia 30%.

The starting compounds and the reagents employed in the process of the present invention are known compounds or can be obtained from known compounds using well known methods.

In particular, the dialkyl acetal of formula (II), when not commercially available, may be prepared with different methods well known to the experts in the art.

For example, the preparation of N-(2,2-dimethoxyethyl) acetamide is described below.

The beta-ketoester or a salt thereof of formula (III), when not commercially available, may be prepared with different methods according to references in the literature. For instance, acid homologation to beta-keto esters may be achieved from acyl chlorides or carboxylic acids by activation with 2,2-dimethyl-1,3-dioxane-4,6-dione (the Meldrum's acid) as described in *J.Med.Chem.* 2001, 44, 90; from acyl chlorides and ethyl hydrogen malonate as reported in *J.Het.Chem.* 1990, 27, 1609; from aryl ethanones with diethylcarbonate as shown in *Can.J.Chem.* 1992, 1323; or from disubstituted benzoic acids by reaction with commercially available malonates of formula (IX) wherein M is a metal such as potassium and R3 is as defined above, in presence of a condensing agent as reported in *Synthetic Communications* 1990, 20, 773.

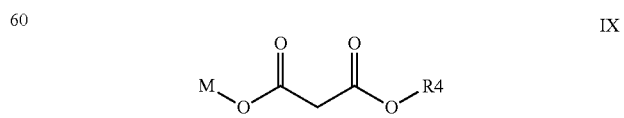

For example, the preparation of ethyl 3-(2,4-dichlorophenyl)-3-oxopropanoate imidazole salt is described below.

The following examples illustrate but do not limit the invention.

Preparation of the starting materials.

A) N-(2,2-dimethoxyethyl)acetamide (II, R3=R4=CH$_3$)

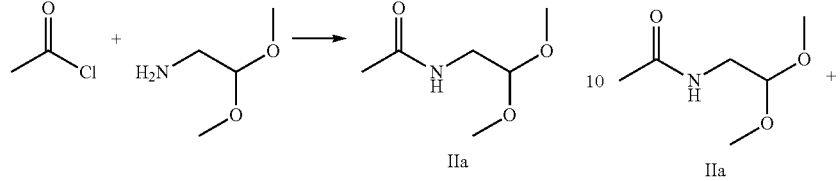

8.2 mL of acetyl chloride were added to a solution of 150 ml of ethyl acetate, 11.2 mL of 2,2-dimethoxyethanamine and 21 mL of triethyl amine at room temperature. After 1 hour, 1.5 mL of ethanol were added. The resulting suspension was stirred for a further hour, and then filtered. Ethyl acetate was removed by evaporation from the filtration liquors yielding the title compound as an oil, which was used without further purifications. H$^1$-NMR (DMSOd$_6$), δ ppm: 7.85 (s broad, 1H); 4.30 (t; 1H); 3.25 (s, 6H); 3.10 (t, 2H); 1.80 (s, 3H).

B) Ethyl 3-(2,4-dichlorophenyl)-3-oxopropanoate imidazole salt (III, R1=R2=Cl, R5=ethyl)

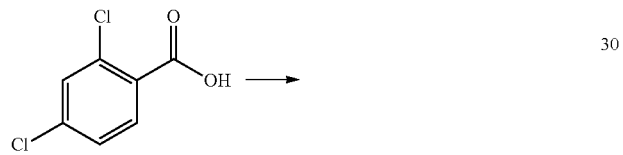

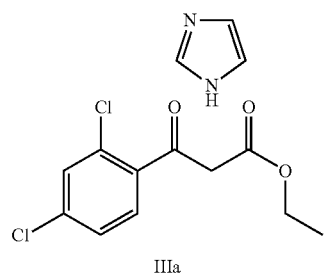

In a reactor cooled at 20° C., 3.76 Kg of carbonyl diimidazole in 5 L of DMF were added to a solution of 4 Kg of 2,4-dichloro-benzoic acid in 25 L of DMF. After 2 hours, 2.4 Kg of MgCl$_2$ and 7.16 Kg of potassium mono ethyl malonate were added. The mixture was heated to 100° C. under stirring until reaction was complete (monitored by HPLC), then cooled to room temperature and dripped in 80 L of water affording the precipitation of a solid.

The solid was then recovered by filtration yielding 8.33 Kg of the title compound, which was used without further purifications.

H$^1$-NMR (DMSOd$_6$), δ ppm: 7.65 (s, 1H); 7.55 (s, 1H); .,4 (s, 2H); 7.1 (s broad, 1H); 6.9 (s broad, 1H); 4.7 (s, 1H); 4.0 (q, 1H); 1.15 (t, 3H).

EXAMPLE 1

Step a)
Ethyl 2-(2,4-dichlorophenyl)-1H-pyrrole-3-carboxylate (IV, R$_1$=R$_2$=Cl, R5=ethyl)

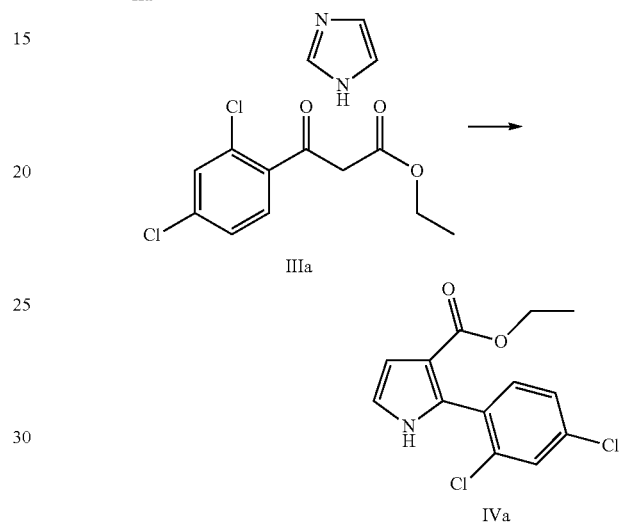

To the amount of oil (IIa), obtained in the preparation A), were added 31 g of ethyl 3-(2,4-dichlorophenyl)-3-oxopropanoate imidazole salt (IIIa), obtained as reported above, and 30 mL of TFA. The reaction mixture was heated for 60 minutes at 60° C., then TFA was removed by evaporation and the oily residue was dissolved in 450 mL of ethyl acetate, washed twice with 300 mL of water and then with 300 mL of a NaHCO$_3$ saturated solution. The organic layer was recovered and the solvent was evaporated yielding dark oil. The oil was treated with 100 mL of ethanol and 50 mL of a 2N solution of NaOH, the resulting reaction mixture was stirred at room temperature over night, then filtered to yield the title compound as a white to yellowish solid (7.2 g).

H$^1$-NMR (DMSOd$_6$), δ ppm: 7.7 (d, 1H); 7.45 (dd, 1H); 7.4 (d, 1H); 6.87 (d, 1H); 6.5 (d, 1H); 4.0 (q, 2H); 1.0 (t, 3H). The same procedure was repeated to obtain the necessary amount of the title compound having the same physicochemical properties.

Step b)
Ethyl 5-acetyl-2-(2,4-dichlorophenyl)-1 H-pyrrole-3-carboxylate(V, R1=R2=Cl; R5=ethyl)

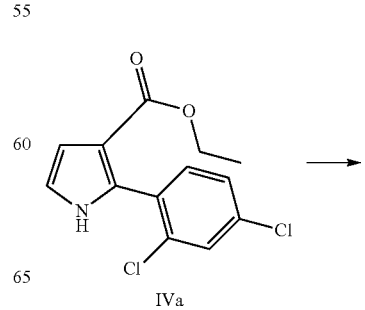

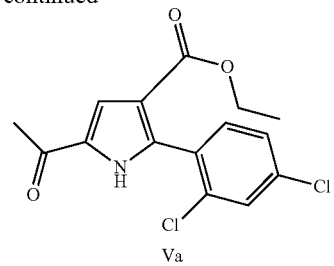

Va

In a round bottom flask at room temperature, 11.8 g of ethyl 2-(2,4-dichlorophenyl)-1H-pyrrole-3-carboxylate (IVa) were dissolved in 230 mL of dichloromethane obtaining a yellow suspension. 4.72 mL of acetyl chloride were then added to the yellow suspension, followed by 16.5 g of AlCl$_3$, observing the formation of a red solution. After 30 minutes the reaction was complete and the reaction mixture was dripped in 230 mL of a 2N solution of HCl under vigorous stirring keeping the temperature below 40° C. The final heterogeneous mixture was cooled at 4° C. for 2 hours, then filtered and the resulting solid was washed with 20 ml of water yielding a first crop of 9.4 g of the title compound.

The organic layer was separated from the biphasic mother liquors and reduced to small volume by evaporation. The resulting oil was treated with 20 mL of ethanol and cooled to −20° C. for 1 hour. A second crop was obtained by filtration yielding 2.1 g of the title compound. The two crops were combined to provide 11.5 g of the title compound, which was used without further purification.

H$^1$-NMR (DMSOd$_6$), δ ppm: 7.57 (d, 1H); 7.45 (s, 1H); 7.41 (dd, 1H); 7.37 (d, 1H); 4.10 (q, 2H); 1.1 (t, 3H).

Step c)

Ethyl 2-(2,4-dichlorophenyl)-5-[3-(dimethylamino)prop-2-enoyl]-1H-pyrrole-3-carboxylate (VI, R1=R2=Cl; R5=ethyl)

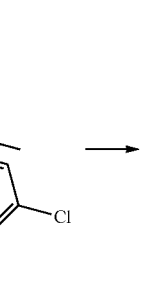

Va

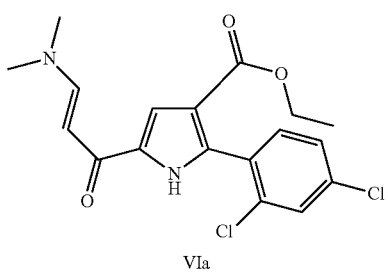

VIa

To 10.6 g of ethyl 5-acetyl-2-(2,4-dichlorophenyl)-1H-pyrrole-3-carboxylate (V) were added 37 mL of dioxane and 27 mL of diisopropyl acetal of N,N-dimethylformamide. The reaction mixture was heated at 95° C. for 12 hours, then cooled to room temperature and filtered. The solid was washed three times with 10 ml of dioxane yielding 11.7 g of the title compound as a white solid, which was used without further purifications.

H$^1$-NMR (DMSOd$_6$), δ ppm:7.7 (d, 1H); 7.6 (d, 1H); 7.45 (dd, 1H); 7.40 (d, 1H); 7.2 (s, 1H); 5.75 (d, 1H); 4.0 (q, 2H); 3.1 (s broad, 3H); .2.9 (s broad, 3H); 1.05 (t, 3H).

The same procedure was repeated to obtain the necessary amount of the title compound having the same physicochemical properties.

Step d)

Ethyl 5-(2-aminopyrimidin-4-yl)-2-(2,4-dichlorophenyl)-1H-pyrrole-3-carboxylate (VII, R1=R2=Cl; R5=ethyl)

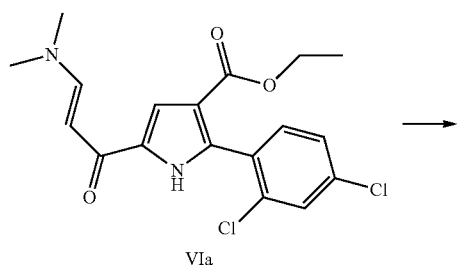

VIa

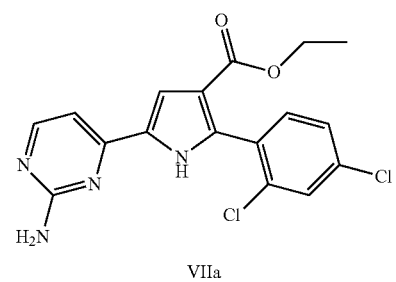

VIIa 12.9 g of ethyl 2-(2,4-dichlorophenyl)-5-[3-(dimethylamino)prop-2-enoyl]-1H-pyrrole-3-carboxylate (VIa) were dissolved in 200 mL of ethanol. 8.1 g of guanidine hydrochloride and 28 mL of EtONa in EtOH 21% w/w were added and the resulting solution was stirred at reflux temperature for 24 h. Ethanol was evaporated and the residue was dissolved in 200 mL of ethyl acetate. The organic phase was washed with 200 mL of water, then with 200 ml of an aqueous solution (96% water, 1.5% acetic acid, 2.5% brine). The organic layer was then concentrated by evaporation to small volume and was cooled at 4° C. for 2 hours. The solid was recovered by filtration yielding 8.9 g of the title compound. Mother liquors were reduced by filtration to small volume and 20 mL of pentane were added; the mixture was cooled at 4° C. for 2 hours and then filtered, affording 1.6 g of the title compound as a white to yellowish solid. The two crops were combined to provide 10.5 g of the title compound which was used without further purification.

H$^1$-NMR (DMSOd$_6$), δ ppm: 8.20 (d, 1H); 7.71 (s broad, 1H); 7.48 (s, 2H); 7.27 (s, 1H); 7.00 (d, 1H); 6.40 (s broad, 2H); 4.02 (q, 2H); 1.05 (t, 3H).

Step e)
(2-Aminopyrimidin-4-yl)-2-(2,4-dichlorophenyl)-1H-pyrrole-3-carboxylic acid (VIII, R1=R2=Cl)

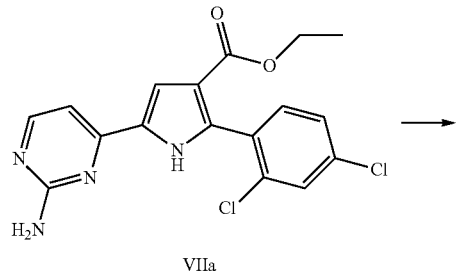

VIIa

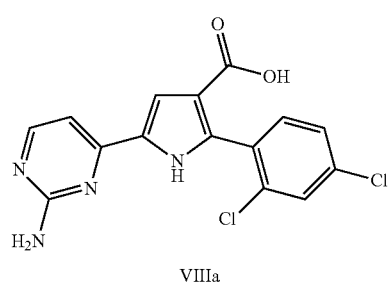

VIIIa 10.5 g of ethyl 5-(2-aminopyrimidin-4-yl)-2-(2,4-dichlorophenyl)-1H-pyrrole-3-carboxylate (VIIa) were treated with 80 ml of dioxane, 100 ml of water and 10 ml of a solution of NaOH 35% w/w. The mixture was heated at reflux temperature for 8 hours. 100 ml of ethyl acetate and 100 ml of water were then added. The aqueous phase was separated and its pH adjusted to 6 by adding a 6N solution of HCl, then filtered to yield the title compound (10.1 g) as a light yellow solid, which was used without further purification.

$^1$H NMR (DMSO-$d_6$/400 MHz) δ ppm: 8.2 (d, 1H); 7.7 (m, 1H); 7.46 (s broad, 2H); 7.2 (s, 1H); 6.95 (d, 1H); 6.4 (s broad, 2H)

MS: m/z 347 [M-H$^+$].

Step f)

(2-Aminopyrimidin-4-yl)-2-(2,4-dichlorophenyl)-1H-pyrrole-3-carboxylic acid amide (I, R1=R2=Cl)

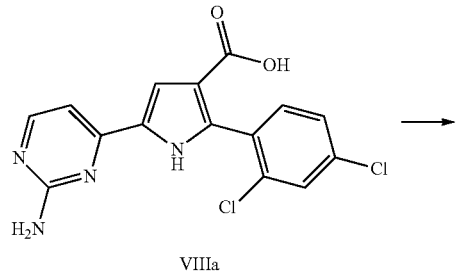

VIIIa

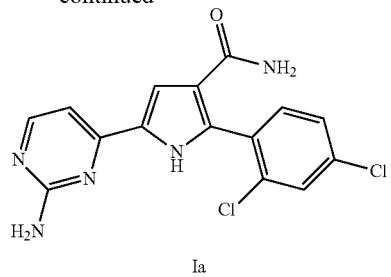

Ia

A solution of 9.3 g of carbonyl diimidazole in 80 mL of dioxane was dripped into a mixture of 10.1 g of (2-aminopyrimidin-4-yl)-2-(2,4-dichlorophenyl)-1H-pyrrole-3-carboxylic acid (VIIIa) in 50 mL of dioxane at 60° C.

Further 4.9 g of carbonyl diimidazole were added in three portions to the reaction mixture at 60° C.

The reaction was allowed to cool at room temperature, then 15 mL of a 30% w/w solution of NH$_3$ in water were added and the reaction mixture was stirred for three days at room temperature. The solid was recovered by filtration and washed with 15 mL of a solution composed by NH$_3$ 30% w/w in water, water and dioxane in 1:1:1 ratio yielding 8.1 g of the title compound as a yellow solid.

$^1$H NMR (DMSO-$d_6$/400 MHz) δ ppm 6.81 (bs, 1H) 6.95 (bs, 2H) 7.01 (d, J=5.73 Hz, 1H) 7.37 (bs, 1H) 7.46 (d, J=2.68 Hz, 1H) 7.68 (dd, J=1.77, 0.55 Hz, 1H) 8.23 (d, J=5.73 Hz, 1H) 12.17 (bs, 1H); ESI (+) MS: m/z 348 (MH$^+$).

EXAMPLE 2

Operating as described in steps a-f of Example 1, and starting from the appropriately substituted beta-ketoester or a salt thereof of the formula (III, R1=R2=H);

(III, R1=CH$_3$, R2=H);

(III, R1=R2=CH$_3$);

(III, R1=R2=F);

(III, R1=Cl, R2=H);

(III, R1=Cl, R2=F);

(III, R1=Cl, R2=OCH$_3$) and (III, R1=F, R2=Cl).

the following compounds were respectively obtained:
5-(2-amino-pyrimidin-4-yl)-2-phenyl-1H-pyrrole-3-carboxylic acid amide;
5-(2-amino-pyrimidin-4-yl)-2-o-tolyl-1H-pyrrole-3-carboxylic acid amide;
5-(2-amino-pyrimidin-4-yl)-2-(4-fluoro-2-methyl-phenyl)-1H-pyrrole-3-carboxylic acid amide;
5-(2-amino-pyrimidin-4-yl)-2-(2,3-dimethyl-phenyl)-1H-pyrrole-3-carboxylic acid amide;
5-(2-amino-pyrimidin-4-yl)-2-(2,3-difluoro-phenyl)-1H-pyrrole-3-carboxylic acid amide;
5-(2-amino-pyrimidin-4-yl)-2-(2,4-difluoro-phenyl)-1H-pyrrole-3-carboxylic acid amide;
5-(2-amino-pyrimidin-4-yl)-2-(2,5-difluoro-phenyl)-1H-pyrrole-3-carboxylic acid amide;

5-(2-amino-pyrimidin-4-yl)-2-(2-chloro-phenyl)-1H-pyrrole-3-carboxylic acid amide;

5-(2-amino-pyrimidin-4-yl)-2-(2-chloro-4-fluoro-phenyl)-1H-pyrrole-3-carboxylic acid amide;

5-(2-amino-pyrimidin-4-yl)-2-(2-fluoro-4-methyl-phenyl)-1H-pyrrole-3-carboxylic acid amide;

5-(2-amino-pyrimidin-4-yl)-2-(2,3-dichloro-phenyl)-1H-pyrrole-3-carboxylic acid amide;

5-(2-amino-pyrimidin-4-yl)-2-(2-fluoro-3-methoxy-phenyl)-1H-pyrrole-3-carboxylic acid amide and 5-(2-amino-pyrimidin-4-yl)-2-(2-fluoro-4-chloro-phenyl)-1H-pyrrole-3-carboxylic acid amide.

The invention claimed is:

1. A process for preparing a 5-(2-amino-pyrimidin-4-yl)-2-aryl-1H-pyrrole-3-carboxamide of the formula (I):

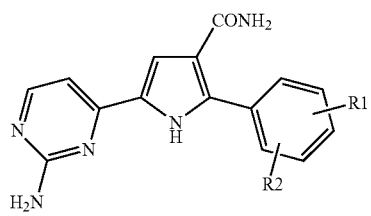

wherein R1 and R2 independently represent hydrogen, halogen, $C_1$-$C_6$ alkyl, ($C_1$-$C_6$) alkoxy, cycloalkyl, aryl or nitro group, which process comprises:

a) coupling an acetal of formula (II):

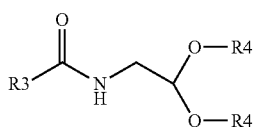

wherein R3 is $C_1$-$C_6$ alkyl and both R4 are independently $C_1$-$C_6$ alkyl or taken together are an alkylene chain having 2 or 3 carbon atoms and forming a cyclic acetal, with a beta-ketoester or a salt thereof of formula (III):

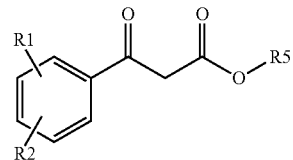

wherein R5 is $C_1$-$C_6$ alkyl, first under acidic conditions and then under nucleophilic conditions;

b) acetylating the resultant compound of the formula (IV):

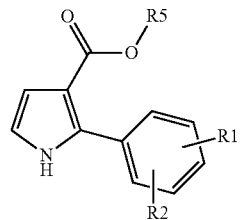

with an acetyl halide or acetic anhydride in the presence of a Lewis acid;

c) reacting the resultant compound of formula (V):

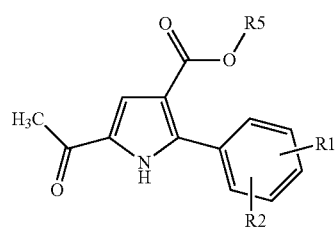

with a $C_1$-$C_6$ dialkyl acetal of N,N-dimethyl formamide;

d) reacting the resultant enaminone of formula (VI):

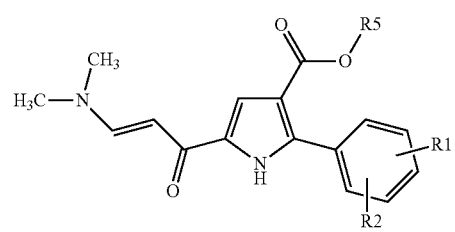

with guanidine or a salt thereof;

e) hydrolyzing the carboxylic ester group of the resultant compound of formula (VII):

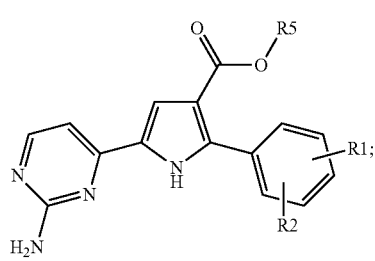

f) condensing the carboxylic acid group of the resultant compound of formula (VIII):

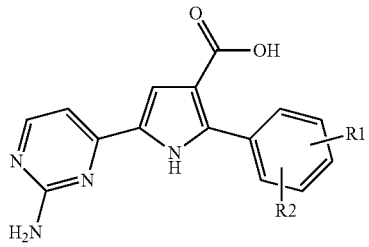

with a form of ammonia, to give the carboxamide of formula (I); and, optionally, converting it into a pharmaceutically acceptable salt.

2. The process for preparing a compound of formula (IV) as defined in claim 1 which process comprises coupling a dialkyl acetal of formula (II) with a beta-ketoester or a salt thereof of formula (III), first under acidic conditions and then under nucleophilic conditions.

3. The process according to claim 1, characterized in that the coupling is performed under strong acidic conditions using trifluoroacetic acid as solvent, at a temperature of from room temperature to reflux temperature; then the reaction mixture is treated under nucleophilic conditions in a hydroalcoholic solution.

4. The process according to claim 1, characterized in that the beta-ketoester is an imidazole salt.

5. An intermediate compound of formula (V):

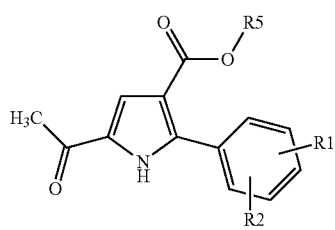

wherein R1 and R2 independently represent hydrogen, halogen, $C_1$-$C_6$ alkyl, ($C_1$-$C_6$) alkoxy, cycloalkyl, aryl or nitro group, and R5 is $C_1$-$C_6$ alkyl.

6. The process for preparing a compound of formula (V) as defined in claim 5, which process comprises the treatment of a compound of the formula (IV):

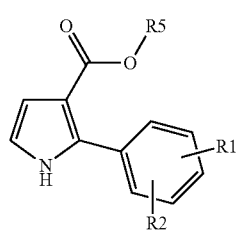

with an acetyl halide or acetic anhydride in the presence of a Lewis acid.

7. The process according to claim 1, characterized in that the acetylation is performed with acetyl chloride in the presence of a Lewis acid, operating at a temperature of from −5° C. to room temperature in an organic solvent.

8. An intermediate enaminone of formula (VI):

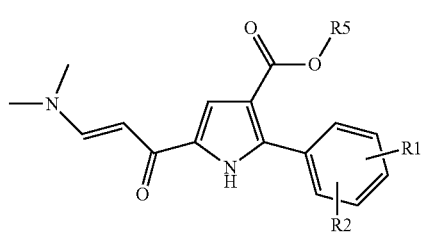

wherein R1 and R2 independently represent hydrogen, halogen, $C_1$-$C_6$ alkyl, ($C_1$-$C_6$) alkoxy, cycloalkyl, aryl or nitro group, and R5 is $C_1$-$C_6$ alkyl.

9. The process for preparing a compound of formula (VI) as defined in claim 8, which process comprises:

a) coupling an acetal of formula (II):

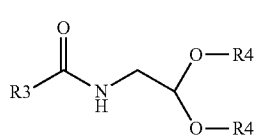

wherein R3 is $C_1$-$C_6$ alkyl and both R4 are independently $C_1$-$C_6$ alkyl or taken together are an alkylene chain having 2 or 3 carbon atoms and forming a cyclic acetal, with a beta-ketoester or a salt thereof of formula (III):

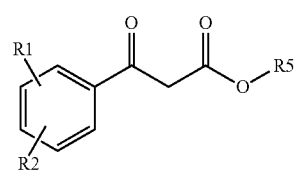

wherein R5 is $C_1$-$C_6$ alkyl, first under acidic conditions and then under nucleophilic conditions;

b) acetylating the resultant compound of the formula (IV):

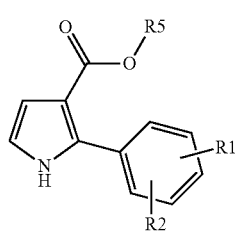

with an acetyl halide or acetic anhydride in the presence of a Lewis acid; and c) reacting the resultant compound of formula (V):

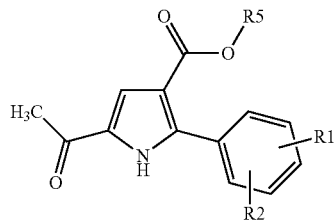

with a $C_1$-$C_6$ dialkyl acetal of N,N-dimethyl formamide.

10. The process for preparing a compound of formula (VI) as defined in claim 8, which process comprises reacting a compound of the formula (V):

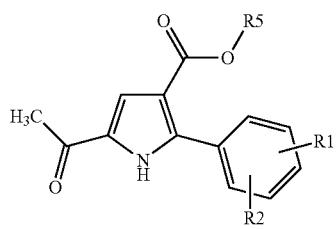

wherein R1 and R2 independently represent hydrogen, halogen, $C_1$-$C_6$ alkyl, ($C_1$-$C_6$) alkoxy, cycloalkyl, aryl or nitro group, and R5 is $C_1$-$C_6$ alkyl with a dialkyl acetal of N,N-dimethylformamide.

11. The process according to claim 1, characterized in that the reaction in step c) is carried out using a dimethyl or diisopropyl acetal of N,N-dimethylformamide at a temperature between room and reflux temperature, in an organic solvent.

12. The process according to claim 1, wherein the compound of formula (I) is:
   5-(2-amino-pyrimidin-4-yl)-2-phenyl-1H-pyrrole-3-carboxylic acid amide;
   5-(2-amino-pyrimidin-4-yl)-2-o-tolyl-1H-pyrrole-3-carboxylic acid amide;
   5-(2-amino-pyrimidin-4-yl)-2-(4-fluoro-2-methyl-phenyl)-1H-pyrrole-3-carboxylic acid amide;
   5-(2-amino-pyrimidin-4-yl)-2-(2,3-dimethyl-phenyl)-1H-pyrrole-3-carboxylic acid amide;
   5-(2-amino-pyrimidin-4-yl)-2-(2,3-difluoro-phenyl)-1H-pyrrole-3-carboxylic acid amide;
   5-(2-amino-pyrimidin-4-yl)-2-(2,4-difluoro-phenyl)-1H-pyrrole-3-carboxylic acid amide;
   5-(2-amino-pyrimidin-4-yl)-2-(2,5-difluoro-phenyl)-1H-pyrrole-3-carboxylic acid amide;
   5-(2-amino-pyrimidin-4-yl)-2-(2-chloro-phenyl)-1H-pyrrole-3-carboxylic acid amide;
   5-(2-amino-pyrimidin-4-yl)-2-(2-chloro-4-fluoro-phenyl)-1H-pyrrole-3-carboxylic acid amide;
   5-(2-amino-pyrimidin-4-yl)-2-(2,4-dichloro-phenyl)-1H-pyrrole-3-carboxylic acid amide;
   5-(2-amino-pyrimidin-4-yl)-2-(2-fluoro-4-methyl-phenyl)-1H-pyrrole-3-carboxylic acid amide;
   5-(2-amino-pyrimidin-4-yl)-2-(2,3-dichloro-phenyl)-1H-pyrrole-3-carboxylic acid amide;
   5-(2-amino-pyrimidin-4-yl)-2-(2-fluoro-3-methoxy-phenyl)-1H-pyrrole-3-carboxylic acid amide or
   5-(2-amino-pyrimidin-4-yl)-2-(2-fluoro-4-chloro-phenyl)-1H-pyrrole-3-carboxylic acid amide.

13. The process according to claim 1, wherein the compound of formula (I) is:
   5-(2-amino-pyrimidin-4-yl)-2-(2,4-dichloro-phenyl)-1H-pyrrole-3-carboxylic acid amide.

14. The process according to claim 6, characterized in that the acetylation is performed with acetyl chloride in the presence of a Lewis acid, operating at a temperature of from −5° C. to room temperature in an organic solvent.

15. The process according to claim 9, characterized in that the reaction in step c) is carried out using a dimethyl or diisopropyl acetal of N,N-dimethylformamide at a temperature between room and reflux temperature, in an organic solvent.

16. The process according to claim 11, wherein said organic solvent is dioxane.

17. The process according to claim 15, wherein said organic solvent is dioxane.

* * * * *

UNITED STATES PATENT AND TRADEMARK OFFICE
CERTIFICATE OF CORRECTION

PATENT NO. : 8,592,583 B2
APPLICATION NO. : 13/505357
DATED : November 26, 2013
INVENTOR(S) : Matteo D'Anello et al.

It is certified that error appears in the above-identified patent and that said Letters Patent is hereby corrected as shown below:

On the Title Page, Item (73) should read:

(73) Assignee: Nerviano Medical Sciences S.r.l., Nerviano (MI) (IT)

Signed and Sealed this
First Day of April, 2014

Michelle K. Lee
*Deputy Director of the United States Patent and Trademark Office*